US010414927B2

(12) United States Patent
Zhou et al.

(10) Patent No.: US 10,414,927 B2
(45) Date of Patent: Sep. 17, 2019

(54) POLYMERIC PHOTO ACTIVE AGENTS

(71) Applicant: Hewlett-Packard Development Company, L.P., Fort Collins, CO (US)

(72) Inventors: Zhang-Lin Zhou, San Diego, CA (US); Or Brandstein, San Diego, CA (US); Rodney David Stramel, San Diego, CA (US); Gregg A. Lane, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 105 days.

(21) Appl. No.: 15/540,130

(22) PCT Filed: Jan. 27, 2015

(86) PCT No.: PCT/US2015/013003
§ 371 (c)(1),
(2) Date: Jun. 27, 2017

(87) PCT Pub. No.: WO2016/122454
PCT Pub. Date: Aug. 4, 2016

(65) Prior Publication Data
US 2017/0369720 A1 Dec. 28, 2017

(51) Int. Cl.
| C08F 2/46 | (2006.01) |
| C08F 2/50 | (2006.01) |
| C08G 61/04 | (2006.01) |
| C09D 11/101 | (2014.01) |
| C09D 11/38 | (2014.01) |
| C09D 11/54 | (2014.01) |
| C07D 335/16 | (2006.01) |

(52) U.S. Cl.
CPC .......... *C09D 11/101* (2013.01); *C07D 335/16* (2013.01); *C09D 11/38* (2013.01); *C09D 11/54* (2013.01)

(58) Field of Classification Search
CPC ....... C09D 11/101; C09D 11/54; C09D 11/38; C07D 335/16
USPC .............. 522/53, 49, 6, 189, 184, 1; 520/1
See application file for complete search history.

(56) References Cited

U.S. PATENT DOCUMENTS

| 4,180,644 A | 12/1979 | Marquis et al. |
| 4,328,322 A | 5/1982 | Baron |
| 4,418,138 A | 11/1983 | Curtis |
| 4,450,279 A | 5/1984 | Shirosaki et al. |
| 4,459,416 A | 7/1984 | Curtis et al. |
| 4,505,794 A | 3/1985 | Kvita et al. |
| 4,602,097 A | 7/1986 | Curtis |
| 5,047,455 A | 9/1991 | Hesse et al. |
| 5,278,310 A | 1/1994 | Raspanti |
| 5,907,046 A | 5/1999 | Bearson et al. |
| 6,011,078 A | 1/2000 | Reich et al. |
| 6,025,408 A | 2/2000 | Williams et al. |
| 6,433,038 B1 | 8/2002 | Tanabe et al. |
| 7,011,699 B2 | 3/2006 | Yamanouchi et al. |
| 7,335,782 B2 | 2/2008 | Herlihy et al. |
| 7,470,015 B2 | 12/2008 | Fukushige |
| 7,541,406 B2 | 6/2009 | Banning et al. |
| 7,683,102 B2 | 3/2010 | Odell et al. |
| 7,790,245 B2 | 9/2010 | Oyanagi et al. |
| 7,837,776 B2 | 11/2010 | Avci et al. |
| 7,994,232 B2 | 8/2011 | Hanawa et al. |
| 8,110,610 B2 | 2/2012 | Loccufier et al. |
| 8,124,666 B2 | 2/2012 | Kito et al. |
| 8,128,843 B2 | 3/2012 | Umebayashi et al. |
| 8,344,038 B2 | 1/2013 | Loccufier et al. |
| 8,366,818 B2 | 2/2013 | Umebayashi |
| 8,389,769 B2 * | 3/2013 | Loccufier ............. C07C 217/22 427/487 |
| 8,562,123 B2 | 10/2013 | Hayata et al. |
| 8,604,095 B2 | 12/2013 | Kagose et al. |
| 8,662,652 B2 | 3/2014 | Mochizuki et al. |
| 8,664,291 B2 | 3/2014 | Kida et al. |
| 8,691,885 B2 | 4/2014 | Okamoto et al. |
| 8,883,873 B2 | 11/2014 | Loccufier et al. |
| 8,946,449 B2 | 2/2015 | Madsen et al. |
| 2002/0198289 A1 | 12/2002 | Gummeson |
| 2004/0209976 A1 | 10/2004 | Nakhmanovich |
| 2006/0142414 A1 | 6/2006 | Hudd |
| 2006/0213393 A1 | 9/2006 | Avci et al. |
| 2007/0123642 A1 | 5/2007 | Banning et al. |
| 2007/0129457 A1 | 6/2007 | Nakano et al. |
| 2008/0024577 A1 | 1/2008 | Nakano et al. |

(Continued)

FOREIGN PATENT DOCUMENTS

| CN | 1594369 | 3/2005 |
| CN | 1594399 | 3/2005 |

(Continued)

OTHER PUBLICATIONS

Oohayashi et al, JP 04026687 Machine Translation, Jan. 29, 1992 (Year: 1992).*
Jie et al, CN 101665575 Machine Translation, Mar. 10, 2010 (Year: 2010).*
Loccufier, EP 2684876 Machine Translation, Jan. 5, 2014 (Year: 2014).*
International Search Report and Written Opinion dated Sep. 10, 2015 for PCT/US2015/013003, Applicant Development Company, L.P. Hewlett-Packard.
Akat et al., Poly(ethylene glycol)-Thioxanthone Prepared by Diels-Alder Click Chemistry as One-Component Polymeric Photoinitiator for Aqueous Free-Radical Polymerization, Journal of Polymer Science: Part A: Polymer Chemistry DOI 10.1002/POLA, 2010, pp. 2109-2114.

(Continued)

*Primary Examiner* — Jessica Whiteley
(74) *Attorney, Agent, or Firm* — Thorpe North & Western LLP

(57) ABSTRACT

The present disclosure is drawn to polymeric photo active agents, photo curable inks containing the polymeric photo active agents, and methods of making the photo curable inks. A polymeric photo active agent can include a xanthone analog modified with a polyether chain connecting to the xanthone analog through an amide linkage.

15 Claims, No Drawings

(56) References Cited

U.S. PATENT DOCUMENTS

| | | |
|---|---|---|
| 2008/0081119 A1 | 4/2008 | Oyanagi et al. |
| 2008/0096998 A1 | 4/2008 | Oyanagi et al. |
| 2008/0122914 A1 | 5/2008 | Toma et al. |
| 2009/0088491 A1 | 4/2009 | Hanawa et al. |
| 2009/0183649 A1 | 7/2009 | Avci et al. |
| 2009/0186163 A1 | 7/2009 | Umebayashi et al. |
| 2009/0197988 A1 | 8/2009 | Kito et al. |
| 2010/0048756 A1 | 2/2010 | Loccufier et al. |
| 2010/0304149 A1* | 12/2010 | Loccufier .................. C08F 2/48 428/412 |
| 2011/0015294 A1 | 1/2011 | Kito et al. |
| 2011/0028586 A1 | 2/2011 | Kito et al. |
| 2011/0144017 A1 | 6/2011 | Dorwald |
| 2011/0195198 A1 | 8/2011 | Loccufier et al. |
| 2012/0147095 A1 | 6/2012 | Miura et al. |
| 2012/0274717 A1 | 11/2012 | Nakano et al. |
| 2012/0293589 A1 | 11/2012 | Hiraoka |
| 2013/0010039 A1 | 1/2013 | Kida et al. |
| 2013/0012611 A1 | 1/2013 | Davidson et al. |
| 2013/0063535 A1 | 3/2013 | Yoda et al. |
| 2013/0237628 A1 | 9/2013 | Casiraghi et al. |
| 2014/0285568 A1 | 9/2014 | Loccufier et al. |

FOREIGN PATENT DOCUMENTS

| | | | |
|---|---|---|---|
| CN | 101665575 | * | 3/2010 |
| CN | 102250059 | | 11/2011 |
| EP | 2684876 | * | 1/2014 |
| JP | 04026687 | * | 1/1992 |
| JP | H08151404 | | 6/1996 |
| JP | 2014227344 | | 12/2014 |
| WO | 0240464 | | 5/2002 |
| WO | 2008061954 | | 5/2008 |
| WO | 2009087862 | | 7/2009 |
| WO | 2011030089 | | 3/2011 |
| WO | 2012003644 | | 1/2012 |
| WO | 2013146061 | | 10/2013 |
| WO | 2013146062 | | 10/2013 |
| WO | 2014158288 | | 10/2014 |

OTHER PUBLICATIONS

Cesur et al., Difunctional monomeric and polymeric photoinitiators: Synthesis and photoinitiating behaviors, Progress in Organic Coatings 86, 2015, pp. 71-78.

Gilman et al., Orientation in the 10-Thiaxanthenone Nucleus, Contribution from the Chemical Laboratory of Iowa State College, vol. 24, 1959, pp. 1914-1916.

Hammick et al., A New Synthesis of 1-Amino-4-methylthioxanthone and of Miracil D., Journal of the Chemical Society (Resumed), 1952, pp. 1077-1080.

Qiu et al., Water-Soluble and Polymerizable Thioxanthone Photoinitiator Containing Imidazole, Journal of Applied Polymer Science, DOI:10.1002/APP.40659, 2014, 6 pages.

Nazir et al., Donor-Acceptor Type Thioxanthones: Synthesis, Optical Properties, and Two-Photon Induced Polymerization, American Chemical Society, DOI:10.1021/acs.macromol5b00336, 2015, 7 pages.

Sharp, A New Synthesis of Lucanthone (Miracil D, Nilodin), Journal of the Chemical Society (Resumed), 1951, pp. 2961-2963.

Wen et al., Amphipathic hyperbranched polymeric thioxanthone photoinitiators (AHPTXs): Synthesis, characterization and photoinitiated polymerization, Polymer 50, 2009, pp. 3917-3923.

Yin-Zhi et al., Synthesis and Crystal Structure of 2-hydroxyl-4-methyl-thioxanthone, Frontiers of Materials, Chemical and Metallurgical Technologies, Advanced Materials Research Vols 581-582, 2012, pp. 189-192.

Zhu et al., Synthesis and Characterization of Highly Efficient Thioxanthone-Based Macrophotoinitiator, Scientific Journal of Materials Science, vol. 2, Issue 4, 2012, pp. 1-8.

Dhif et al., Synthesis of 2,3-Crown-Ethers and 2,2'-Linked Dimers From Hydroxy-Substituted Acridinones, Synthetic Communications, 21 (8&9), pp. 969-975, 1991.

* cited by examiner

POLYMERIC PHOTO ACTIVE AGENTS

BACKGROUND

Recently, curing of ink by radiation, and in particular ultraviolet (UV) curing, has become popular. UV curable ink can be cured after printing by application of UV light. Typically, UV curable inks include monomers that form polymers by free radical polymerization. The growing end of each polymer chain is a radical that reacts with additional monomers, transferring the radical to the end of the chain as each monomer is added. A photo initiator is used to form the first radicals to begin the polymerization process. The photo initiator is capable of absorbing UV light to generate radicals to react with the monomers.

Two types of photo initiators can be used in UV curable compositions. Type I photo initiators are unimolecular photo initiators that undergo a hemolytic bond cleavage upon absorption of UV light, forming radicals. Type II photo initiators are bimolecular photo initiators. These are used as a system of a photo initiator with a synergist, which can together form radicals upon exposure to UV light. Some type II photo initiators react by hydrogen abstraction from the synergist to the photo initiator.

DETAILED DESCRIPTION

The present disclosure is drawn to polymeric photo active agents that can be used as photo initiators, sensitizers, or both. More specifically, the present disclosure provides polymeric photo active agents comprising a xanthone analog modified with a polyether chain connecting to the xanthone analog through an amide linkage. The polymeric photo active agents can be water soluble and stable in aqueous inks, such as aqueous thermal inkjet inks, for example. The polymeric photo active agents also resist migration in the ink after curing. Thus, the polymeric photo active agents of the present disclosure overcome some of the drawbacks of other photo initiators and sensitizers which do not behave in this positive manner in aqueous systems. Some small molecular weight photo initiators, such as isopropyl thioxanthone (ITX), can have unwanted odor, toxicity, and migration in cured materials. On the other hand, many polymeric photo initiators are not water soluble and are difficult to formulate into aqueous inks. Furthermore, some polymeric photo initiators using other types of linkages, such as ester linkages, are not stable in the basic aqueous conditions that are common in thermal inkjet inks.

The inkjet printing industry uses various types of inks, such as oil-based inks, solvent-based (non-aqueous) inks, water-based (aqueous) inks, and solid inks which are melted in preparation for dispensing. Solvent-based inks are fast drying, and as a result, are widely used for industrial printing. When solvent-based inks containing binders and other ingredients are jetted onto a substrate, the solvent(s) partially or fully evaporate from the ink, leaving the binder and other ingredients such as pigment particles on the printed substrate in the form of a dry film. During the drying process, the solvents, which are often volatile organic compounds (VOC), emit vapors, and therefore, can pollute the environment. The amount of pollution produced can increase greatly with higher printing speeds or for wide format images, where large amounts of ink are deposited onto a substrate. As a result of this and other concerns, efforts related to preparing inks that are environmentally friendly have moved some research in the direction of water-based inks. However, radiation-curable (or photo-curable) water-based ink compositions are noticeably limited among available options due to their specific formulation properties. Accordingly, the development of radiation-curable water-based ink compositions that exhibit, when printed, specific desirable printing properties such as, for example, jetting properties as well as improved adhesion would be an advancement in the field of inkjet technology.

Accordingly, a polymeric photo active agent can include a xanthone analog modified with a polyether chain connecting to the xanthone analog through an amide linkage. As used herein, "xanthone" refers to the chemical compound having the Formula 1:

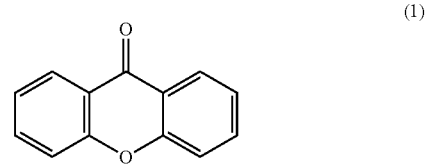 [SMILES: O=c1c2ccccc2oc2ccccc12]

(1)

Also, as used herein, "xanthone analog" refers to xanthone itself and other chemical compounds having the same basic structure as xanthone, but in which one or more atoms are replaced by different atoms or moieties. For example, any of the hydrogen atoms can be replaced by R groups or the ring structures themselves can be replaced by other atoms. In some specific examples, the oxygen atom that is a member of the central ring of the xanthone molecule can be replaced by a sulfur atom or an —NH— group. Thioxanthone is an example of a xanthone analog in which this oxygen atom is replaced by a sulfur atom. As used herein, "thioxanthone" refers to the molecule also called thioxanthen-9-one, having the Formula 2:

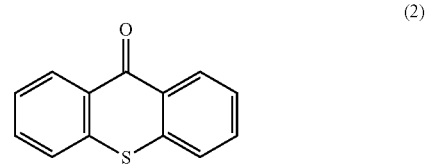 [SMILES: O=c1c2ccccc2sc2ccccc12]

(2)

Other molecules with a similar shape can also be xanthone analogs. Additional examples include compounds having Formulas 3-5:

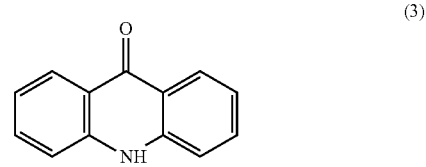

(3)

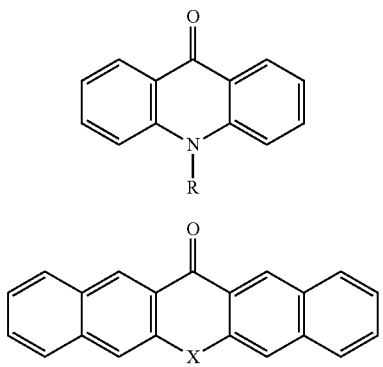

where R (in Formula 4 or 5) is $CH_3$, $CH_2CH_3$, or $CH_2CH_2CH_3$, and X is —O—, —S—, —NH—, or —NR—.

The polyether chain can be a polyglycol, paraformaldehyde, or other polyether. For example, the polyether chain can be polyethylene glycol (PEG), methoxypolyethylene glycol (MPEG), polypropylene glycol (PPG), polybutylene glycol (PBG), or a polyglycol copolymer. In one specific example, the polyether chain can be selected from polyethylene glycol, polypropylene glycol, and a copolymer of polyethylene glycol and polypropylene glycol. In another specific example, the polyether chain can be derived from a portion of a commercially available polyether amine such as Jeffamine® ED-900, Jeffamine® M-1000 (both available from Huntsman Corporation), or others. Various molecular weights of polyether can be suitable. The type of polyether chain and the molecular weight of the polyether chain can in some cases affect the solubility of the final polymeric photo active agent. For example, a higher ratio of oxygen atoms to carbon atoms in the polyether chain tends to make the polymeric photo active agent more soluble. The molecular weight of the polyether chain can also affect the degree to which the polymeric photo active agent can migrate in a cured ink. Longer polyether chains can make it more difficult for the polymeric photo active agent to move within a cured ink, thus decreasing migration. Therefore, the type of polyether chain can be selected to give good water solubility and low migration of the polymeric photo active agent in cured ink. In one example, the polyether chain can be a polyglycol having at least 5 glycol monomer units, and more specifically in one example, from 5 to 200 glycol monomer units.

The polyether chain can connect to the xanthone analog through an amide linkage. As used herein, "amide linkage" refers to either an amide group or an amide group with a bridging group attached to the carbon atom of the amide group. Further, as used herein, connecting the polyether chain to the xanthone analog through an amide linkage means that the polyether chain is directly bonded to the nitrogen atom of the amide group, and the carbon atom of the amide group is either directly bonded or linked through the bridging group to a carbon atom in one of the aromatic side rings of the xanthone analog. This amide linkage can be formed by a suitable reaction, such as a substitution reaction or a condensation reaction.

The xanthone analog, polyether chain, and amide linkage do not necessarily make up the entire polymeric photo active agent. For example, additional groups can be attached along the polyether chain or at the opposite end of the polyether chain. In some cases, one or more additional xanthone analog moieties can be attached to the polyether chain. These additional xanthone analog moieties can connect to the polyether chain through amide linkages. In one example, an additional xanthone analog moiety can connect to an opposite end of the polyether chain through an amide linkage. In other examples, the polyether chain can have multiple branches and each branch can terminate with a xanthone analog moiety connected to the polyether chain through an amide linkage. Specific examples of such polymeric photo active agents are described in detail below.

In some examples, the xanthone analog with the amide linkage can have a general formula according to Formula 6:

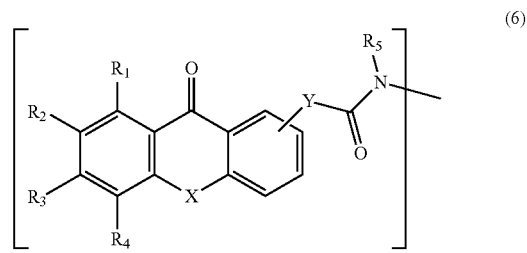

In Formula 6, the amide linkage is illustrated as an amide group with a bridging group Y bonded to the right side ring of the xanthone analog. The amide linkage can be bonded to any of the available carbon atoms in the right side ring by replacing a hydrogen atom. The groups $R_1$, $R_2$, $R_2$, $R_4$, and $R_5$ can be independently a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$, or a perfluoroalkyl group. In this example, $R_d$, $R_e$, and $R_f$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl. In one specific example, $R_1$ to $R_4$ can each be a hydrogen atom. The group X can be —O—, —S—, —NH—, or —NR— where R is $CH_3$, $CH_2CH_3$, or $CH_2CH_2CH_3$. The Y group can be a bond, $(CH_2)_q$ or $O(CH_2)_q$, where q is any integer from 1 to 100. Formula 6 illustrates only the xanthone analog with the amide linkage. A complete polymeric photo active agent can be formed by combining a xanthone analog and amide linkage as in Formula 6 with a polyether chain. The polyether chain can be bonded to the nitrogen atom in the amide linkage.

In some examples, the polymeric photo active agent can have a general formula according one of Formulas 7-10:

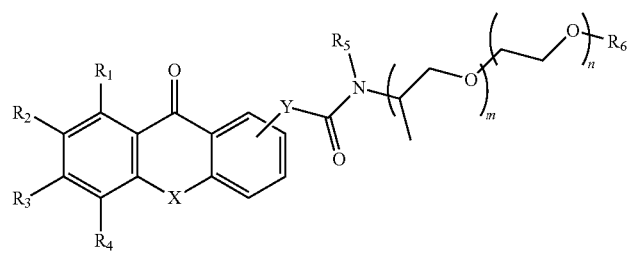
(7)
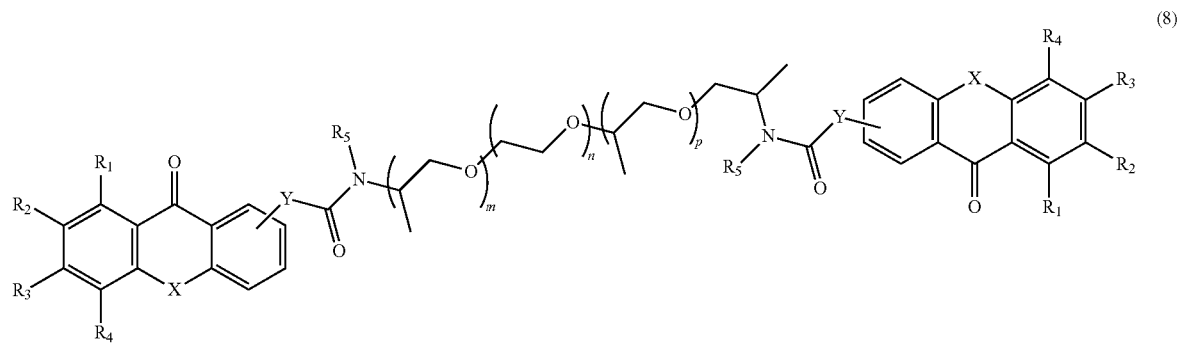
(8)
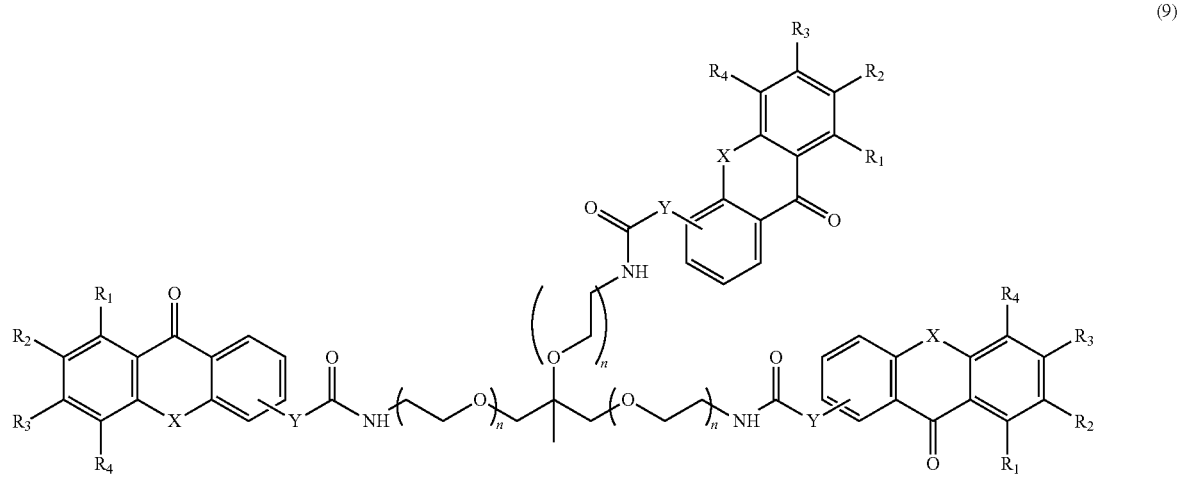
(9)
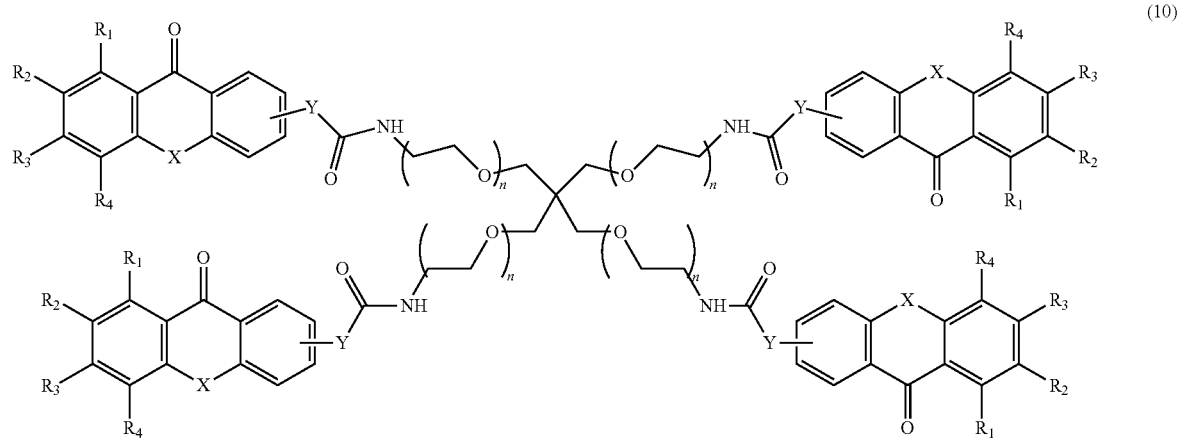
(10)

In each of Formulas 7-10, the groups $R_1$, $R_2$, $R_2$, $R_4$, $R_5$, and $R_6$ can be independently a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$, or a perfluoroalkyl group. In these examples, $R_d$, $R_e$, and $R_f$ are independently a hydrogen atom, an unsubstituted alkyl, a substituted alkyl, an unsubstituted alkenyl, a substituted alkenyl, an unsubstituted aryl, a substituted aryl, an unsubstituted aralkyl, or a substituted aralkyl. In one specific example, $R_1$ to $R_6$ can each be a hydrogen atom. The numbers of monomer units m, n, and p can independently be any integer from 0 to 200, provided that the sum of m, n, and p is at least 5. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$ or $O(CH_2)_q$, wherein q is any integer from 1 to 100.

As shown in Formulas 7-10, the polymeric photo active agent can include 1, 2, 3, or 4 xanthone analog moieties connected to a branching polyether chain. In other examples, the polyether chain can have more than 4 branches terminating in xanthone analog moieties.

In one example, the polymeric photo active agent can have a general formula according to Formula 11:

eneoxy chain portion of a commercially available polyether amine such as Jeffamine® ED-900, Jeffamine® M-1000 (both available from Huntsman Corporation), or others. In polymeric photo active agents having multiple xanthone analog moieties, a smaller molecular weight polyether chain can be used while still maintaining a high overall molecular weight of the polymeric photo active agent. The molecular weight of the polymeric photo active agent can also be changed by adding R groups to the xanthone analog. It is noted that when referring to "R groups" generically herein, this term is defined to include at least H and organic side chain side groups and other specific constituents described and defined elsewhere herein, e.g., R, $R_1$, $R_2$, $R_3$, $R_4$, $R_5$, $R_6$, $R_d$, $R_e$, $R_f$, etc.

The molecular weight of the polymeric photo active agent can also affect its solubility in water. In some cases, the polyether chain can be a water soluble polyether. Although the xanthone analog alone can be insoluble in water, adding the soluble polyether chain can make the entire polymeric photo active agent soluble. In such cases, the soluble polyether can have a sufficient molecular weight so that its solubility properties overcome the insolubility of the xanthone analog. In other cases, water soluble R groups can be added to the xanthone analog to increase the solubility of the polymeric photo active agent. In one example, the polymeric photo active agent can have a water solubility of at least 0.5 wt %.

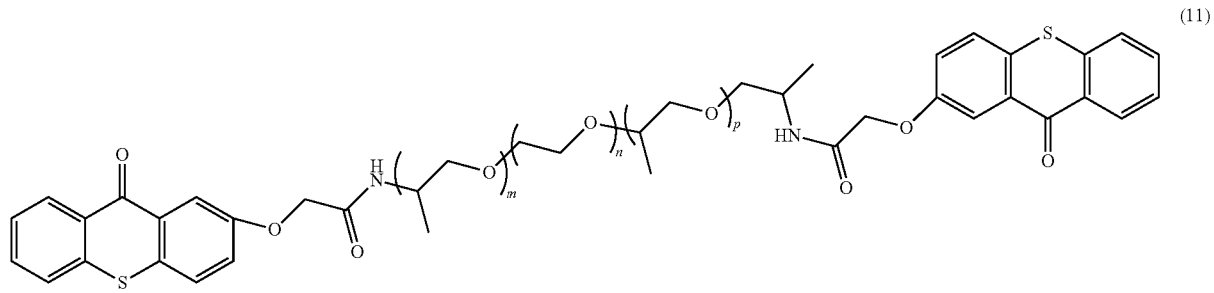

(11)

In the specific example described by Formula 11, m, n, and p can be any integer, e.g, 0 to 200, and in one example, the sum of m, n, and p is from 10 to 25.

The molecular weight of the polymeric photo active agent can affect its degree of migration in cured ink. For example, a polymeric photo active agent with a weight-average molecular weight (Mw) of about 500 Mw or more can have reduced migration in cured ink compared with a small molecule photo initiator or sensitizer. Migration can be further reduced by increasing the molecular weight of the polymeric photo active agent to about 1000 Mw or more. In one example, the polymeric photo active agent can have a molecular weight from about 500 Mw to about 5000 Mw. Polyethers of various molecular weights are available, allowing for the production of polymeric photo active agents with various molecular weights. In some examples, the polyether chain can be selected from PEG 550, PEG 600, and PEG 1000. In another specific example, the polyether chain can be derived from the polyethyleneoxy polypropyl- Typical aqueous ink jet inks can have a pH in the range of 7 to 12. Some commercially available photo initiators and sensitizers with ester linkages can break down in such basic conditions. The amide linkage in the polymeric photo active agents according to the present disclosure can be stable under these conditions. In some examples, the polymeric photo active agent can be stable in water up to a pH from 7 to 12. In other examples, the polymeric photo active agent can be stable in water up to a pH of 8 or higher. As used herein, "stable" refers to the ability of the polymeric photo active agent to have a shelf life of at least 1 year. Typically, aqueous ink jet inks can have a shelf life of greater than 1 year, greater than 2 years, or longer.

A general pathway for forming a polymeric photo active agent in accordance with an example of the present disclosure is shown in Formula 12:

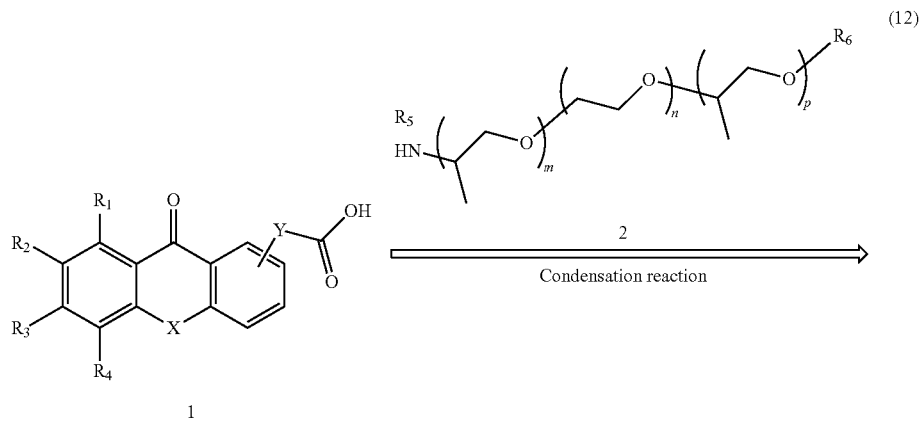

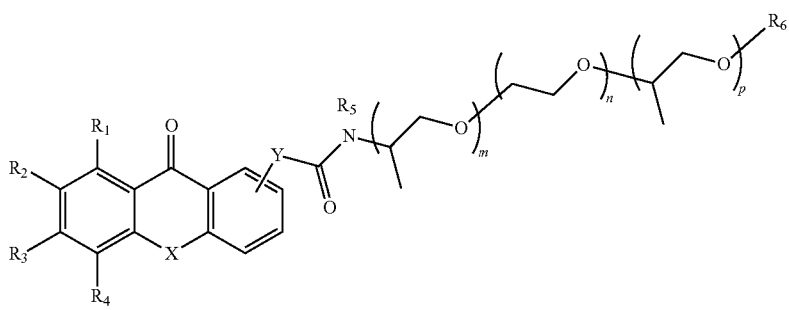

In the pathway shown in Formula 12, $R_1$ to $R_6$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units m, n, and p can be any integer from 0 to 200, provided that the sum of m, n, and p is at least 5. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with a polyethyleneoxy polypropyleneoxy amine (2) in the presence of a coupling reagent such as N,N'-dicyclohexylcarbodiimide (DCC) or 1,1'-carbonyldiimidazole (CDI) to give the desired polymeric photo active agent. Lines leading to the center of aromatic rings in the acid derivative xanthone analog (1) and the final polymeric photo active agent signify that the group can be attached at any available location on the ring.

An alternate example of a general pathway for forming a polymeric photo active agent in accordance with the present disclosure is shown in Formula 13:

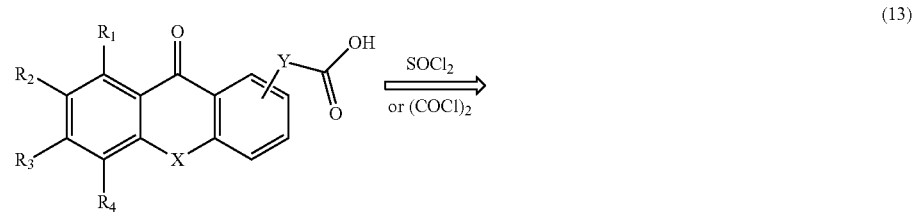

-continued

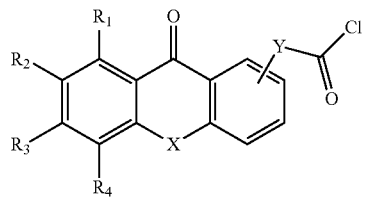

3

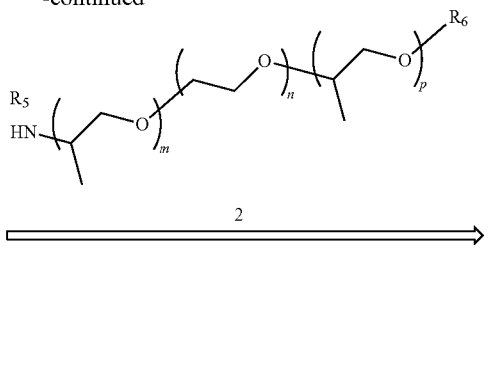

2

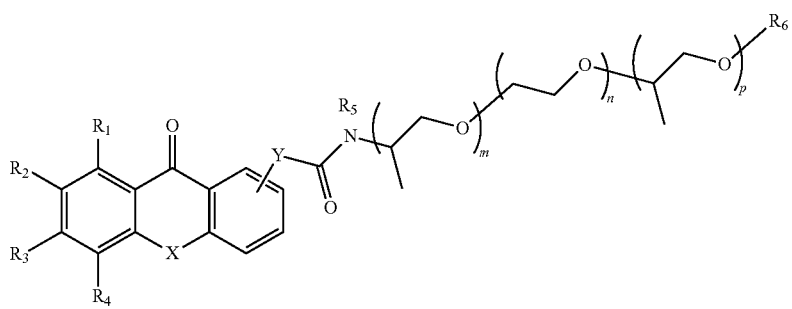

In the pathway shown in Formula 13, $R_1$ to $R_6$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units m, n, and p can be any integer from 0 to 200, provided that the sum of m, n, and p is at least 5. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with either thionyl chloride or oxalyl chloride to give an acid chloride derivative xanthone analog (3). Treatment of the acid chloride (3) with the polyethyleneoxy polypropyleneoxy amine (2) gives the desired polymeric photo active agent. Lines leading to the center of aromatic rings in the acid derivative xanthone analog (1), the acid chloride derivative xanthone analog (3), and the final polymeric photo active agent signify that the group can be attached at any available location on the ring.

A further example of a general pathway for forming a polymeric photo active agent in accordance with the present disclosure is shown in Formula 14:

(14)

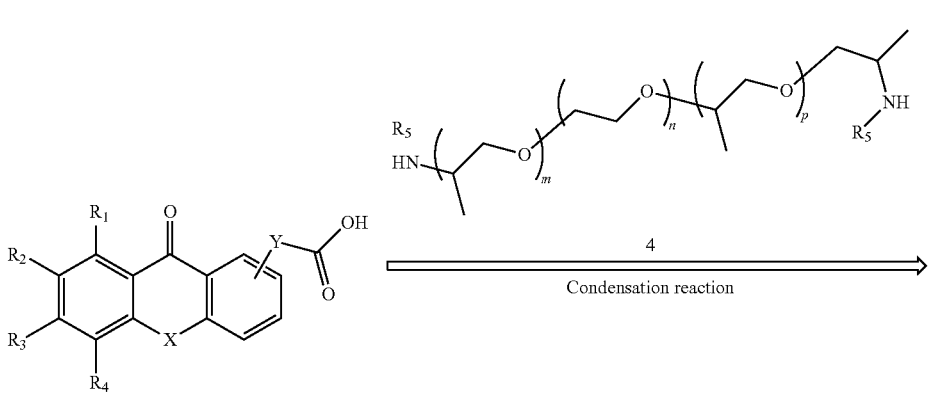

-continued

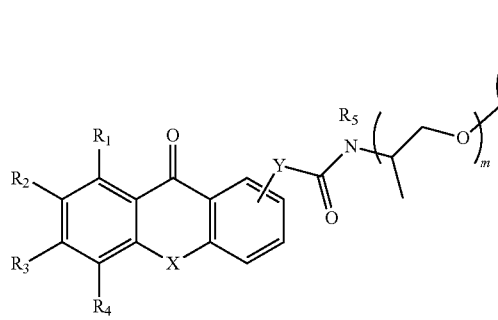 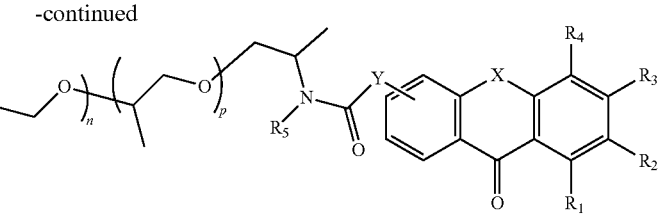

In the pathway shown in Formula 14, $R_1$ to $R_5$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units m, n, and p can be any integer from 0 to 200, provided that the sum of m, n, and p is at least 5. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with a polyethyleneoxy polypropyleneoxy diamine (4) in the presence of a coupling reagent such as DCC or CDI to give the desired polymeric photo active agent having two xanthone analog moieties. Lines leading to the center of aromatic rings in the acid derivative xanthone analog (1) and the final polymeric photo active agent signify that the group can be attached at any available location on the ring Yet another example of a general pathway for forming a polymeric photo active agent in accordance with the present disclosure is shown in Formula 15:

(15)

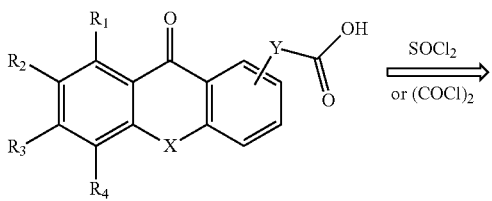 

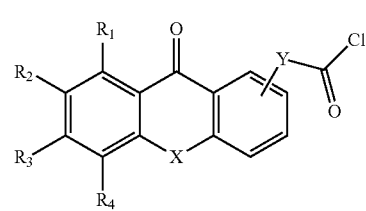 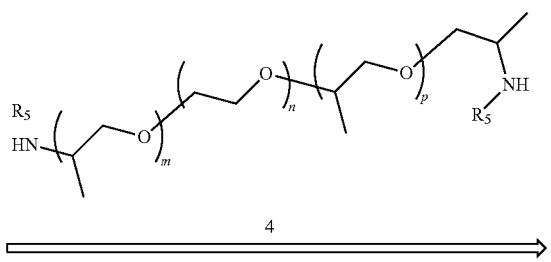

-continued

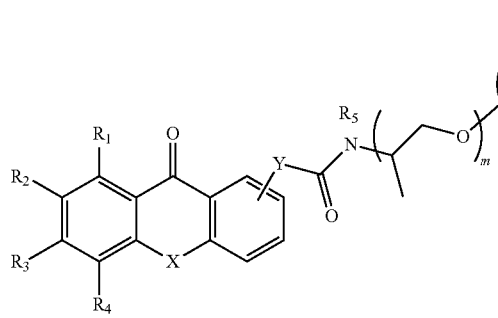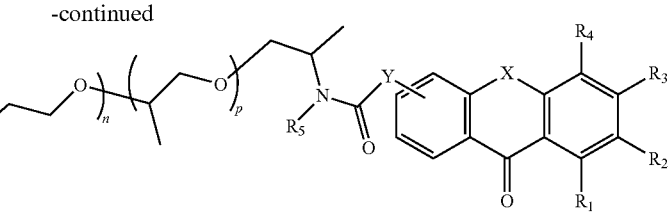

In the pathway shown in Formula 15, $R_1$ to $R_5$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units m, n, and p can be any integer from 0 to 200, provided that the sum of m, n, and p is at least 5. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with either thionyl chloride or oxalyl chloride to give an acid chloride derivative xanthone analog (3). Treatment of the acid chloride (3) with the polyethyleneoxy polypropyleneoxy diamine (4) gives the desired polymeric photo active agent having two xanthone analog moieties. Lines leading to the center of aromatic rings in the acid derivative xanthone analog (1), the acid chloride derivative xanthone analog (3), and the final polymeric photo active agent signify that the group can be attached at any available location on the ring.

An additional example of a general pathway for forming a polymeric photo active agent in accordance with the present disclosure is shown in Formula 16:

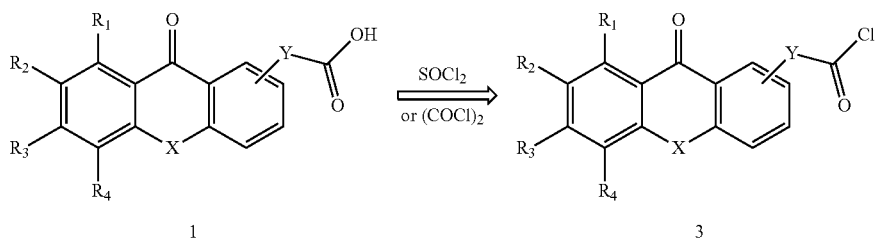

(16)

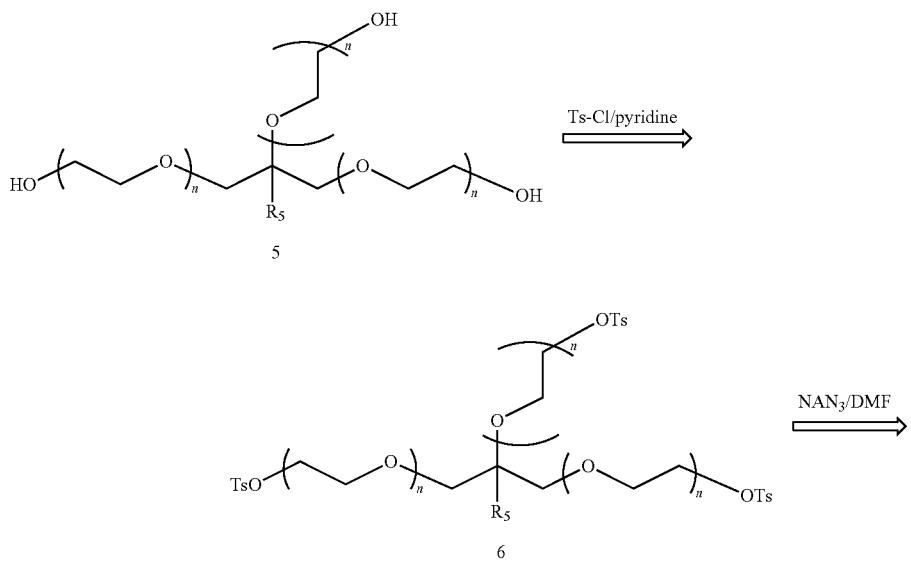

-continued

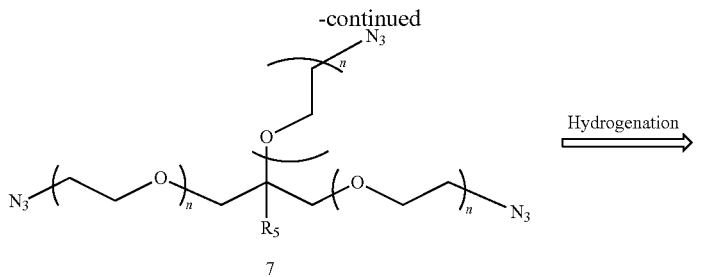

7

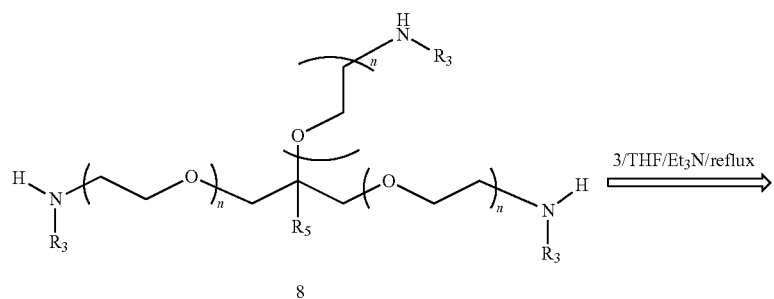

8

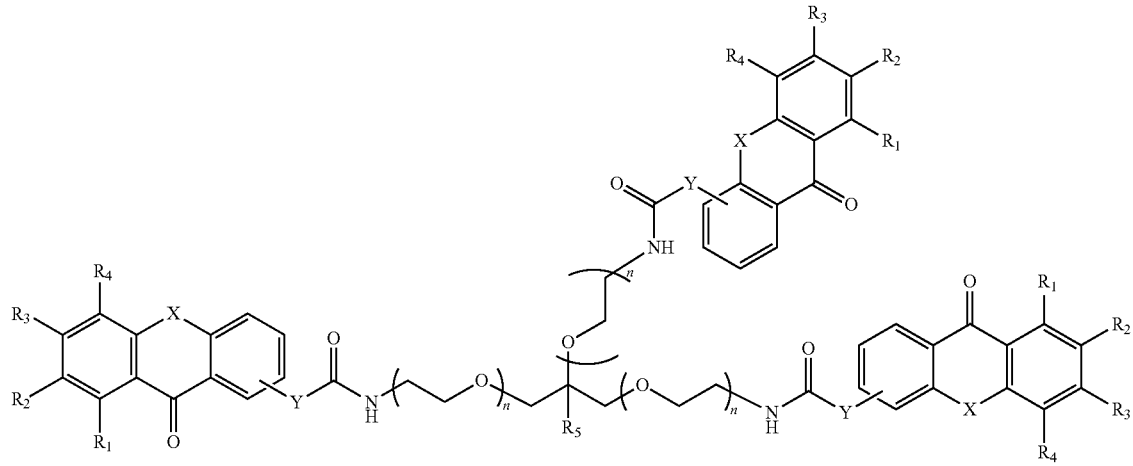

50

In the pathway shown in Formula 16, $R_1$ to $R_5$ each independently represent a hydrogen atom, a substituted or unsubstituted alkyl, alkenyl, aryl or aralkyl group or a group selected from a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units n can be any integer from 5 to 200. The group X can be $-O-$, $-S-$, $-NH-$, or $-NR-$ where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with either thionyl chloride or oxalyl chloride to give an acid chloride derivative xanthone analog (3). A glycerol polyethylene glycol derivative (5) is reacted with toluenesulfonyl chloride in pyridine to give the corresponding tosylate compound (6). Treating the tosylate compound (6) with sodium azide gives the corresponding azide (7). Hydrogenation of the azide (7) gives the corresponding triamine (8). The triamine (8) reacts with the acid chloride derivative xanthone analog (3) to give the desired polymeric photo active agent having three xanthone analog moieties. Lines leading to the center of aromatic rings in the acid derivative xanthone analog (1), the acid chloride derivative xanthone analog (3), and the final polymeric photo active agent signify that the group can be attached at any available location on the ring.

Yet another example of a general pathway for forming a polymeric photo active agent in accordance with the present disclosure is shown in Formula 17:

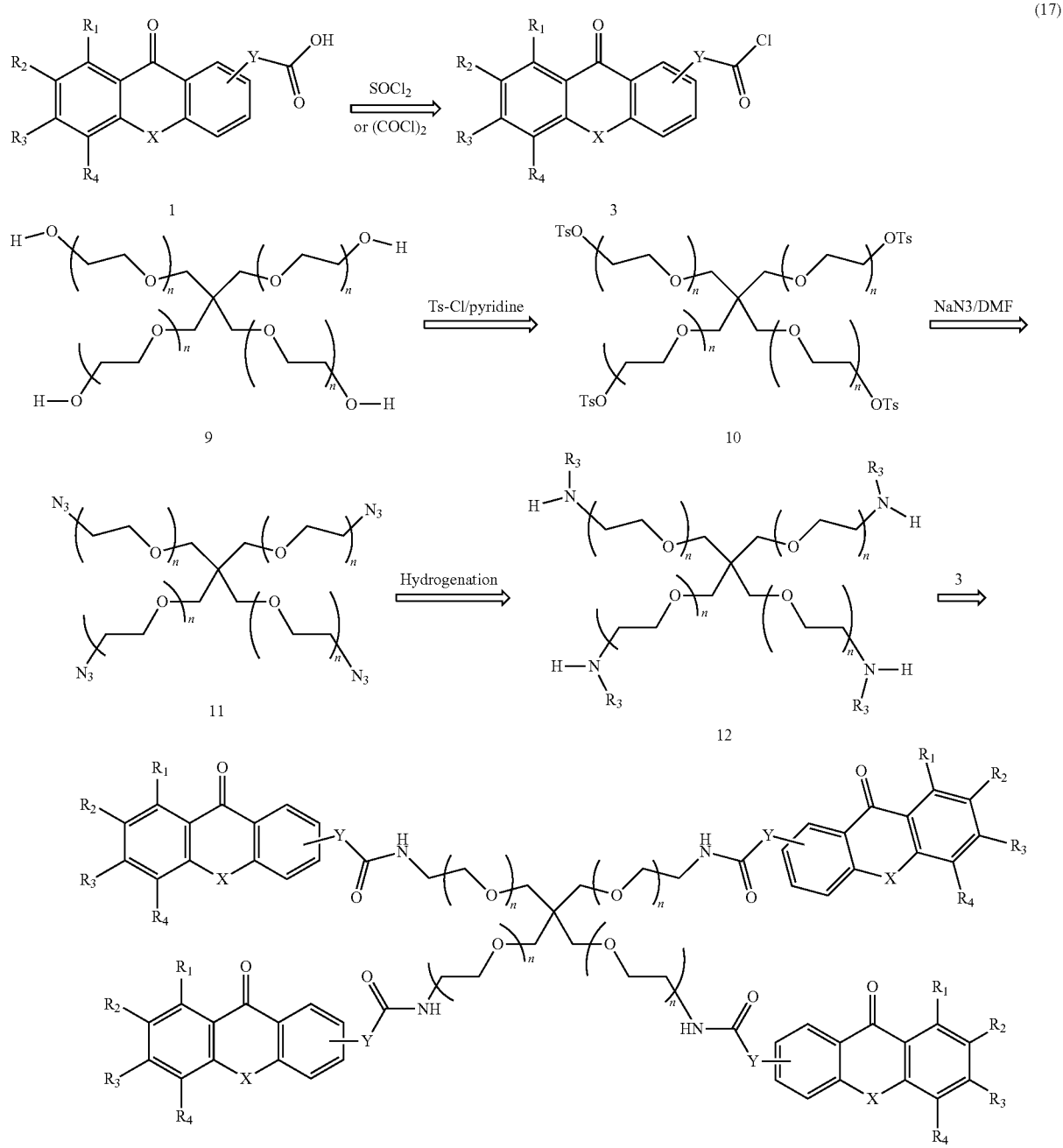

(17)

In the pathway shown in Formula 17, $R_1$ to $R_4$ each independently represent a hydrogen atom, a substituted or unsubstituted alkyl, alkenyl, aryl or aralkyl group or a group selected from a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—R, —$NR_d$—CO—$NR_eR_f$, —$SR_d$, —SO—$R_d$, —$SO_2$—$R_d$, —$SO_2$—O—$R_d$, —$SO_2NR_dR_e$ or a perfluoroalkyl group. $R_d$, $R_e$ and $R_f$ independently represent a hydrogen or a substituted or unsubstituted alkyl, alkenyl, aryl or aralkyl group. The numbers of monomer units n can be any integer from 5 to 200. The group X can be —O—, —S—, —NH—, or —NR— where R is $CH_3$, $CH_2CH_3$, or $CH_2CH_2CH_3$. The Y group can be a bond, $(CH_2)_q$, or $O(CH_2)_q$, wherein q is any integer from 1 to 100.

According to this pathway, an acid derivative xanthone analog (1) is reacted with either thionyl chloride or oxalyl chloride to give an acid chloride derivative xanthone analog (3). A pentaerythritol polyethylene glycol derivative (9) is reacted with toluenesulfonyl chloride in pyridine to give the corresponding tosylate compound (10). Treating the tosylate compound (10) with sodium azide gives the corresponding azide (11). Hydrogenation of the azide (11) gives the corresponding tetraamine (12). The tetraamine (12) reacts with the acid chloride derivative xanthone analog (3) to give the desired polymeric photo active agent having four xanthone analog moieties. Lines leading to the center of aromatic rings in the acid derivative xanthone analog (1), the acid chloride derivative xanthone analog (3), and the final polymeric photo active agent signify that the group can be attached at any available location on the ring Formula 18 illustrates a detailed synthetic pathway for one example of a polymeric photo active agent in accordance with the present disclosure:

According to this pathway, phenol (14) and 2-thiosalicylic acid (12) undergo a condensation reaction in concentrated sulfuric acid under heated conditions to yield 2-hydroxythioxanthen-9-one (15). The 2-hydroxythioxanthen-9-one is treated with sodium hydroxide in THF under reflux to give the corresponding sodium salt (16). Reaction of the sodium salt (16) with ethyl bromoacetate (17) gives the corresponding ester (18), which is hydrolyzed to form acid (19).

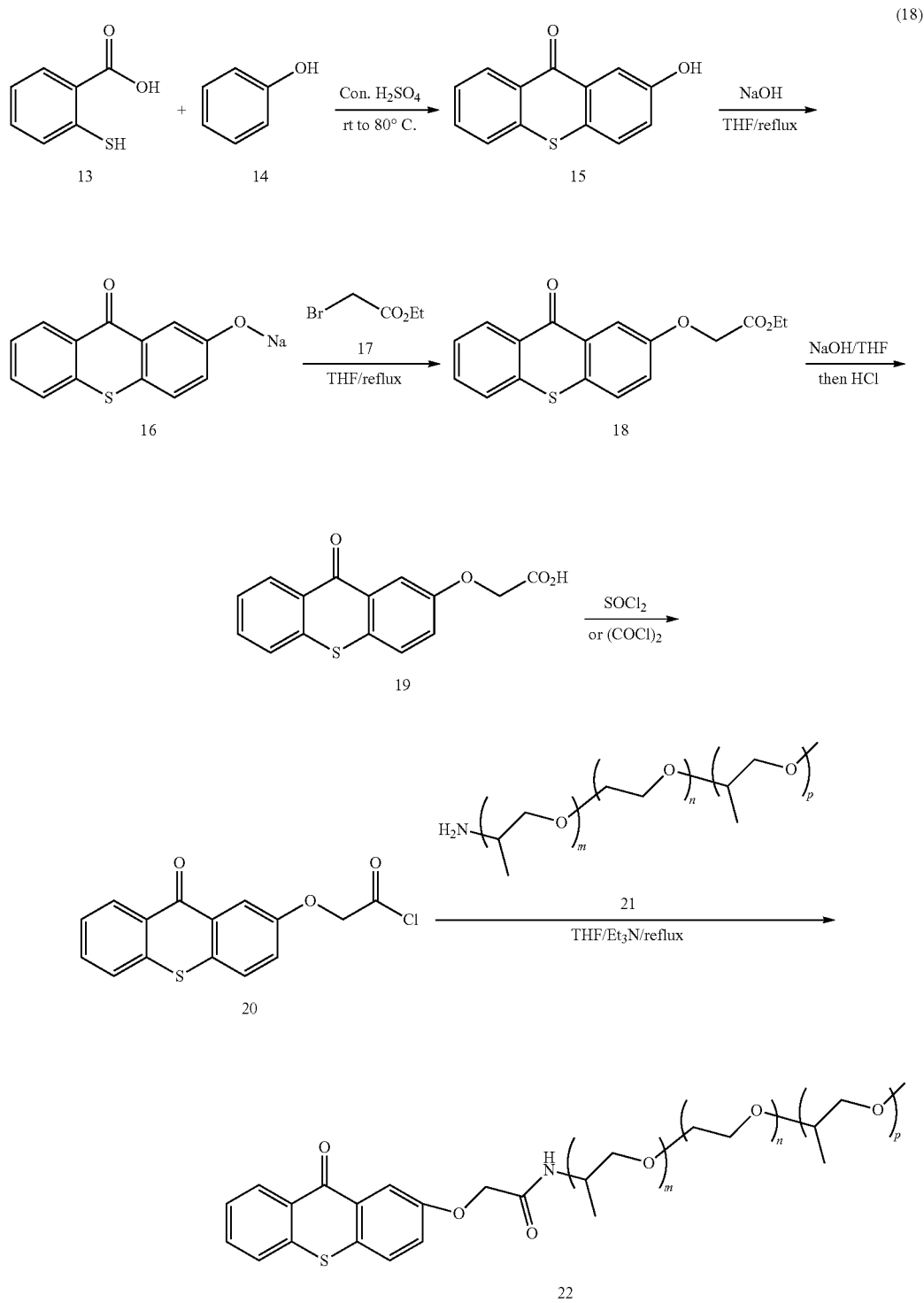

(18)

Reacting the acid (19) with thionyl chloride under reflux gives the corresponding acid chloride (20). Reaction of the acid chloride (20) with a polyethyleneoxy polypropyleneoxy monomethyl ether amine (21) gives the desired polymeric photo active agent (22).

A detailed synthetic pathway for another example of a polymeric photo active agent in accordance with the present disclosure is shown in Formula 19:

The polymeric photo active agents of the present disclosure can act as type II photo initiators. Therefore, the photo curable ink can include a synergist so that the photo initiator and synergist together can generate radicals during photo curing, such as with UV curing or even LED curing processes. In some examples, the synergist can be an amine synergist. The amine synergist can be a tertiary amine compound. In one example, the amine synergist can be a

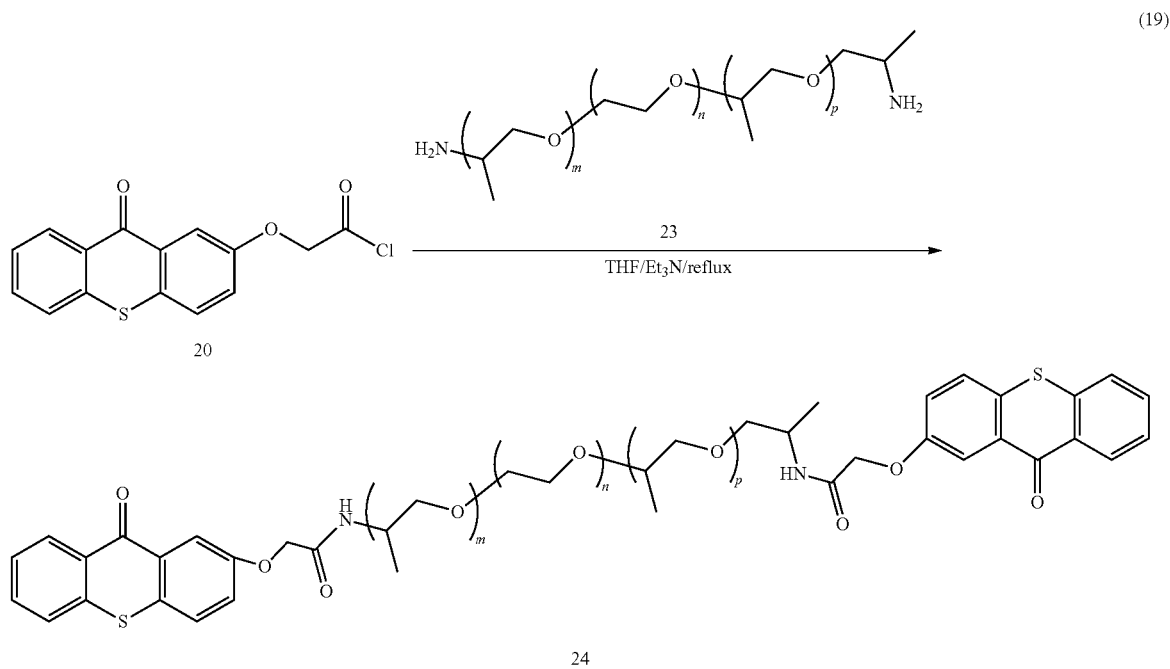

(19)

In this pathway, an acid chloride (20) is reacted with a polyethyleneoxy polypropyleneoxy diamine (23) to give the desired polymeric photo active agent (24).

The present disclosure also extends to photo curable inks, such as UV curable inks including LED curable inks. In some examples, a photo curable ink can include a photo reactive binder (such as a UV curable or LED curable binder), a polymeric photo active agent, a co-photo initiator and/or a synergist, a colorant, a co-solvent, and water. The polymeric photo active agent can be a xanthone analog modified with a polyether chain connecting to the xanthone analog through an amide linkage. In various aspects, the polymeric photo active agent can act as a photo initiator with the synergist, or it can act as a sensitizer for a co-photo initiator, for example.

In some cases, the photo reactive binder can include a UV or LED curable polyurethane and hydrophobic radiation-curable monomers. In one example, the UV reactive binder can include a water dispersible (meth)acrylated polyurethane, such as NeoRad® R-441 by Neo Resins (Avecia). Other examples of UV reactive binders can include Ucecoat® 7710, Ucecoat® 7655 (available from Cytec), Neorad® R-440, Neorad® R-441, Neorad® R-447, Neorad® R-448 (available from DSM NeoResins), Bayhydrol® UV 2317, Bayhydrol® UV VP LS 2348 (available from Bayer), Lux 430, Lux 399, Lux 484 (available from Alberdingk Boley), Laromer® LR 8949, Laromer® LR 8983, Laromer® PE 22WN, Laromer® PE 55WN, Laromer® UA 9060 (available from BASF), or combinations thereof.

polymeric amine synergist such as a derivative of aniline and a polyether amine such as Jeffamine® 900. In other examples, the amine synergist can be trimethylamine, triethanolamine, methyldiethanolamine, phenyldiethanolamine, N,N,N',N'-tetra(hydroxylethyl)ethylenediamine, dimethylaminoethyl acrylate, dimethylaminoethyl methacrylate, ethyl dimethylaminobenzoate, or combinations thereof.

The polymeric photo active agents of the present disclosure can act as the primary photo initiator in the photo curable ink, or they can act as a sensitizer for another photo initiator. Therefore, the photo curable ink can in some cases include a second photo initiator in addition to the polymeric photo active agents disclosed herein. Examples of radical photo initiators include, by way of illustration and not limitation, 1-hydroxy-cyclohexylphenylketone, benzophenone, 2,4,6-trimethylbenzo-phenone, 4-methylbenzophenone, diphenyl-(2,4,6-trimethylbenzoyl)phosphine oxide, phenyl bis(2, 4,6trimethylbenzoyl)phosphine oxide, 2-hydroxy-2-methyl-1-phenyl-1-propanone, benzyl-dimethyl ketal, 2-methyl-I-[4-(methylthio)phenyl]-2-morpholinopropan-1-one, or combinations thereof. Non-limiting examples of additional photo initiators include alpha amino ketone UV photo initiators such as Ciba® Irgacure® 907, Ciba® Irgacure® 369, and Ciba® Irgacure® 379; bis acylphosphine oxide (BAPO) UV photo initiators such as Irgacure® 819, Darocur® 4265, and Darocur® TPO; alpha hydroxy ketone UV photo initiators such as Irgacure® 184 and Darocur® 1173; including photo initiators with or without sensitizers such as Darocur® ITX (2-isopropyl thioxanthone).

The colorant in the photo curable ink can be a pigment, a dye, or a combination thereof. In some examples, the colorant can be present in an amount from 0.5 wt % to 10 wt % in the photo curable ink. In one example, the colorant can be present in an amount from 1 wt % to 5 wt %. In another example, the colorant can be present in an amount from 5 wt % to 10 wt %.

In some examples, the colorant can be a dye. The dye can be nonionic, cationic, anionic, or a mixture of nonionic, cationic, and/or anionic dyes. Specific examples of dyes that can be used include, but are not limited to, Sulforhodamine B, Acid Blue 113, Acid Blue 29, Acid Red 4, Rose Bengal, Acid Yellow 17, Acid Yellow 29, Acid Yellow 42, Acridine Yellow G, Acid Yellow 23, Acid Blue 9, Nitro Blue Tetrazolium Chloride Monohydrate or Nitro BT, Rhodamine 6G, Rhodamine 123, Rhodamine B, Rhodamine B Isocyanate, Safranine O, Azure B, and Azure B Eosinate, which are available from Sigma-Aldrich Chemical Company (St. Louis, Mo.). Examples of anionic, water-soluble dyes include, but are not limited to, Direct Yellow 132, Direct Blue 199, Magenta 377 (available from Ilford AG, Switzerland), alone or together with Acid Red 52. Examples of water-insoluble dyes include azo, xanthene, methine, polymethine, and anthraquinone dyes. Specific examples of water-insoluble dyes include Orasol® Blue GN, Orasol® Pink, and Orasol® Yellow dyes available from Ciba-Geigy Corp. Black dyes may include, but are not limited to, Direct Black 154, Direct Black 168, Fast Black 2, Direct Black 171, Direct Black 19, Acid Black 1, Acid Black 191, Mobay Black SP, and Acid Black 2.

In other examples, the colorant can be a pigment. The pigment can be self-dispersed with a polymer, oligomer, or small molecule; or can be dispersed with a separate dispersant. Suitable pigments include, but are not limited to, the following pigments available from BASF: Paliogen® Orange, Heliogen® Blue L 6901F, Heliogen® Blue NBD 7010, Heliogen® Blue K 7090, Heliogen® Blue L 7101F, Paliogen® Blue L 6470, Heliogen® Green K 8683, and Heliogen® Green L 9140. The following black pigments are available from Cabot: Monarch® 1400, Monarch® 1300, Monarch® 1100, Monarch® 1000, Monarch® 900, Monarch® 880, Monarch® 800, and Monarch® 700. The following pigments are available from CIBA: Chromophtal® Yellow 3G, Chromophtal® Yellow GR, Chromophtal® Yellow 8G, Igrazin® Yellow 5GT, Igralite® Rubine 4BL, Monastral® Magenta, Monastral® Scarlet, Monastral® Violet R, Monastral® Red B, and Monastral® Violet Maroon B. The following pigments are available from Degussa: Printex® U, Printex® V, Printex® 140U, Printex® 140V, Color Black FW 200, Color Black FW 2, Color Black FW 2V, Color Black FW 1, Color Black FW 18, Color Black S 160, Color Black S 170, Special Black 6, Special Black 5, Special Black 4A, and Special Black 4. The following pigment is available from DuPont: Tipure® R-101. The following pigments are available from Heubach: Dalamar® Yellow YT-858-D and Heucophthal Blue G XBT-583D. The following pigments are available from Clariant: Permanent Yellow GR, Permanent Yellow G, Permanent Yellow DHG, Permanent Yellow NCG-71, Permanent Yellow GG, Hansa Yellow RA, Hansa Brilliant Yellow 5GX-02, Hansa Yellow-X, Novoperm® Yellow HR, Novoperm® Yellow FGL, Hansa Brilliant Yellow 10GX, Permanent Yellow G3R-01, Hostaperm® Yellow H4G, Hostaperm® Yellow H3G, Hostaperm® Orange GR, Hostaperm® Scarlet GO, and Permanent Rubine F6B. The following pigments are available from Mobay: Quindo® Magenta, Indofast® Brilliant Scarlet, Quindo® Red R6700, Quindo® Red R6713, and Indofast® Violet. The following pigments are available from Sun Chemical: L74-1357 Yellow, L75-1331 Yellow, and L75-2577 Yellow. The following pigments are available from Columbian: Raven® 7000, Raven® 5750, Raven® 5250, Raven® 5000, and Raven® 3500. The following pigment is available from Sun Chemical: LHD9303 Black. Any other pigment and/or dye can be used that is useful in modifying the color of the UV curable ink. Additionally, the colorant can include a white pigment such as titanium dioxide, or other inorganic pigments such as zinc oxide and iron oxide.

The components of the photo curable ink can be selected to give the ink good ink jetting performance. Besides the photo curable binder, photo reactive photo active agents, and the colorant, the photo curable ink can also include a liquid vehicle. Liquid vehicle formulations that can be used in the photo curable ink can include water and one or more co-solvents present in total at from 1 wt % to 50 wt %, depending on the jetting architecture. Further, one or more non-ionic, cationic, and/or anionic surfactant can be present, ranging from 0.01 wt % to 20 wt %. In one example, the surfactant can be present in an amount from 5 wt % to 20 wt %. The liquid vehicle can also include dispersants in an amount from 5 wt % to 20 wt %. The balance of the formulation can be purified water, or other vehicle components such as biocides, viscosity modifiers, materials for pH adjustment, sequestering agents, preservatives, and the like. In one example, the liquid vehicle can be predominantly water.

Classes of co-solvents that can be used can include organic co-solvents including aliphatic alcohols, aromatic alcohols, diols, glycol ethers, polyglycol ethers, caprolactams, formamides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs ($C_6$-$C_{12}$) of polyethylene glycol alkyl ethers, N-alkyl caprolactams, unsubstituted caprolactams, both substituted and unsubstituted formamides, both substituted and unsubstituted acetamides, and the like. Specific examples of solvents that can be used include, but are not limited to, 2-pyrrolidinone, N-methylpyrrolidone, 2-hydroxyethyl-2-pyrrolidone, 2-methyl-1,3-propanediol, tetraethylene glycol, 1,6-hexanediol, 1,5-hexanediol and 1,5-pentanediol.

One or more surfactants can also be used, such as alkyl polyethylene oxides, alkyl phenyl polyethylene oxides, polyethylene oxide block copolymers, acetylenic polyethylene oxides, polyethylene oxide (di)esters, polyethylene oxide amines, protonated polyethylene oxide amines, protonated polyethylene oxide amides, dimethicone copolyols, substituted amine oxides, and the like. The amount of surfactant added to the formulation of this disclosure may range from 0.01 wt % to 20 wt %. Suitable surfactants can include, but are not limited to, liponic esters such as Tergitol™ 15-S-12, Tergitol™ 15-S-7 available from Dow Chemical Company, LEG-1 and LEG-7; Triton™ X-100; Triton™ X-405 available from Dow Chemical Company; LEG-1, and sodium dodecylsulfate.

Consistent with the formulation of this disclosure, various other additives can be employed to optimize the properties of the ink composition for specific applications. Examples of these additives are those added to inhibit the growth of harmful microorganisms. These additives may be biocides, fungicides, and other microbial agents, which are routinely used in ink formulations. Examples of suitable microbial agents include, but are not limited to, NUOSEPT® (Nudex, Inc.), UCARCIDE™ (Union carbide Corp.), VANCIDE® (R.T. Vanderbilt Co.), PROXEL® (ICI America), and combinations thereof.

Sequestering agents, such as EDTA (ethylene diamine tetra acetic acid), may be included to eliminate the deleterious effects of heavy metal impurities, and buffer solutions may be used to control the pH of the ink. From 0.01 wt % to 2 wt %, for example, can be used. Viscosity modifiers and buffers may also be present, as well as other additives to modify properties of the ink as desired. Such additives can be present at from 0.01 wt % to 20 wt %.

Table 1 shows the composition of an example of a photo curable ink, e.g., UV LED curable ink, formulation in accordance with the present disclosure. The ink can be formulated by mixing these ingredients or by other formulations. The pH of the ink can then be adjusted. In one example, the ingredients can be stirred for 30 minutes, and then aqueous potassium hydroxide can be added to adjust the pH to 7 to 12, or in one example, about 8.5. It is noted that though water concentrations are listed as "balance," it is understood that the balance of components could included other liquid vehicle components or minor amounts of solids often present in inkjet ink compositions.

TABLE 1

| Component | Weight Percent |
|---|---|
| Photo reactive binder (UV reactive polymer) | 1-20% |
| Polymeric photo active agent (sensitizer or photo initiator) | 0.15-5% |
| Co-photo initiator | *0-10% |
| Synergist | *0-5% |
| Surfactant | 0-20% |
| Anti-kogation agent | 0-5% |
| Pigment | 0.5-10% |
| Organic Co-solvent | 0.1-50% |
| Water | remainder |

*As noted, when the polymeric photo active agent is included as a sensitizer, the co-photo initiator is at greater than 0%. When the polymeric photo active agent is included as a photo initiator, the synergist is at greater than 0%. All three components can likewise be present, i.e. the polymeric photo active agent, the co-photo initiator, and the synergist.

The photo curable ink can be used to print on a broad selection of substrates including untreated plastics, flexible as well as rigid, porous substrates such as paper, cardboard, foam board, textile, and others. The ink has a good adhesion on a variety of substrates. The photo curable ink also has a good viscosity, enabling good printing performances and enables the ability to formulate inks suitable for inkjet application. In some examples, the ink can be formulated for thermal inkjet printing. The photo curable ink composition of the present disclosure enables high printing speed and is very well suited for a use in digital inkjet printing.

The polymeric photo active agents of the present disclosure can be stable in aqueous environments at pH from 7 to 12 or higher. Thus, the photo curable ink can be formulated to have a pH from 7 to 12 or higher. In some examples, the photo curable ink can have a pH of 8 or higher. In one specific example, the photo curable ink can have a pH of 8.5.

The polymeric photo active agent can exhibit less migration in cured ink compared with small molecule photo initiators. The photo curable binder in the ink can comprise polymers or monomers that polymerize or cross-link during the curing process. As the binder cures, the polymeric photo active agent can become locked into the cured binder due to the long polyether chain of the polymeric photo active agent. Therefore, the photo curable ink can be formulated so that there is little or no migration of the polymeric photo active agent in the ink after curing.

The present disclosure also extends to a method of making a photo curable ink. The method includes mixing a photo reactive binder, a polymeric photo active agent comprising a xanthone analog modified with a polyether chain connecting to the xanthone analog through an amide linkage, a co-photo initiator, an amine synergist, a colorant, a co-solvent, and water. The photo curable ink can be UV curable, and in one specific example, UV LED curable. In one example, the method can also include adjusting the pH of the ink to be from 7 to 12. In another example, the method can include adjusting the pH of the ink to be 8 or higher.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, "photo active agent" refers to materials that participate in the initiation of photo polymerization, particularly materials that act as a photo initiator or a sensitizer for a photo initiator. The polymeric photo active agents disclosed herein can be used either as a photo initiator or as a sensitizer for another photo initiator. In some systems, the polymeric photo active agent can act as both a photo initiator and a sensitizer.

As used herein, "UV curable" refers to compositions that can be cured by exposure to ultraviolet light from any UV source such as a mercury vapor lamp, UV LED source, or the like. Mercury vapor lamps emit high intensity light at wavelengths from 240 nm to 270 nm and 350 nm to 380 nm. "LED curable" refers to compositions that can be cured either by ultraviolet light from an ultraviolet LED. Ultraviolet LEDs emit light at specific wavelengths. For example, ultraviolet LEDs are available at 365 nm and 395 nm wavelengths, among others. The term "photo curable" refers generally to compositions that can be cured by exposure to light from any wavelength suitable for the composition being cured. Typically, the photo curable composition will be UV curable, and in some cases UV LED curable.

As used herein, "liquid vehicle" or "ink vehicle" refers to a liquid fluid in which colorant is placed to form an ink. A wide variety of ink vehicles may be used with the systems and methods of the present disclosure. Such ink vehicles may include a mixture of a variety of different agents, including, surfactants, solvents, co-solvents, anti-kogation agents, buffers, biocides, sequestering agents, viscosity modifiers, surface-active agents, water, etc.

As used herein, "colorant" can include dyes and/or pigments.

As used herein, "dye" refers to compounds or molecules that absorb electromagnetic radiation or certain wavelengths thereof. Dyes can impart a visible color to an ink if the dyes absorb wavelengths in the visible spectrum.

As used herein, "pigment" generally includes pigment colorants, magnetic particles, aluminas, silicas, and/or other ceramics, organo-metallics or other opaque particles, whether or not such particulates impart color. Thus, though the present description primarily exemplifies the use of pigment colorants, the term "pigment" can be used more generally to describe not only pigment colorants, but other pigments such as organometallics, ferrites, ceramics, etc. In one specific example, however, the pigment is a pigment colorant.

As used herein, "ink-jetting" or "jetting" refers to compositions that are ejected from jetting architecture, such as ink-jet architecture. Ink-jet architecture can include thermal or piezo architecture. Additionally, such architecture can be configured to print varying drop sizes such as less than 10 picoliters, less than 20 picoliters, less than 30 picoliters, less than 40 picoliters, less than 50 picoliters, etc.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following illustrates several examples of the present disclosure. However, it is to be understood that the following are only illustrative of the application of the principles of the present disclosure. Numerous modifications and alternative compositions, methods, and systems may be devised without departing from the spirit and scope of the present disclosure. The appended claims are intended to cover such modifications and arrangements.

Example 1

Synthesis of 2-hydroxythioxanthen-9-one: 2-Mercaptobenzoic acid (61.6 g, 0.4 mol) was added to concentrated sulfuric acid (600 mL) and stirred until uniformly dispersed. Then phenol (188.2 g, 2 mol) was added slowly and proportionwise with stirring, maintaining the temperature below 60° C. After the addition, the mixture was stirred for 1 hour at room temperature and then for 2 hours at 95-100° C. The reaction mixture was allowed to cool to room temperature and then carefully poured into 4.5 L of boiling water. The mixture was stirred and filtered. The filter cake was then washed with water and dried in vacuum, which was then further purified by flash chromatography to give the desired 2-hydroxythioxanthen-9-one (3) (60 g, 60% yield).

Example 2

Synthesis of sodium salt of 2-hydroxythioxanthen-9-one: To a mixture of 2-hydroxythioxanthen-9-one (28.5 g, 0.125 mol) in 300 mL of THF was added sodium hydroxide (30 g, 0.75 mol). The mixture was heated to reflux for 2 hours. After cooling down to room temperature, THF was evaporated off. Then to the flask was added 200 mL of water and the solid was separated by filtration, washed with acetone (2×100 ml) and then hexanes (2×100 ml) and finally dried in an oven overnight, producing the desired sodium salt of 2-hydroxythioxanthen-9-one (28 g, 90% yield).

Example 3

Synthesis of 2-carboxymethoxythioxanthone: To a mixture of 2-hydroxythioxanthone (22.8 g, 0.1 mol) in 300 mL of THF was added sodium hydroxide (24 g, 0.6 mol). The mixture was heated to reflux for 2 hours, during which time the color changed to bright red, indicating the formation of the sodium salt of 2-hydroxythioxanthone. After cooling down to room temperature, ethyl bromoacetate (35.1 g, 0.21 mol) was added and reflux was continued for three hours. After cooling to room temperature, 400 mL of deionized water was added with stirring and then THF was evaporated off to give a clear red solution. Then the solution was allowed to reflux for another 3 hours to hydrolyze all the ester intermediate. Then the solution was cooled to room temperature and acidified by 1N hydrochloric acid to pH 2 with stirring. A yellow solid precipitated out. After refluxing for another 10 min to make sure all the sodium salt was converted to free acid, the mixture was cooled to room temperature and stirred for two hours. The yellow solid was filtered off and washed with water (2×200 mL) and then dried in the oven to give the desired 2-carboxymethoxythioxanthone (28 g, 97% yield).

Example 4

Synthesis of 2-thioxanthonyloxyacetic acid chloride: To a mixture of 2-carboxymethoxythioxanthone (32.7 g, 0.114 mol) in 300 mL of THF was added a solution of thionyl chloride (27.2 g, 0.228 mol) in 50 mL of THF. The resulting mixture was heated to reflux for 24 hours. After cooling down to room temperature, THF and unreacted thionyl chloride was evaporated off by vacuum, giving rise to the desired 2-thioxanthonyloxyacetic acid chloride (35 g, 100% yield). The material was used for next step in Example 5 without further purification.

Example 5

Synthesis of bis-(2-carboxymethoxythioxanthone) derivative of Jeffamine® ED-900: A mixture of 2-thioxanthonyloxyacetic acid chloride (34.7 g, 0.114 mol), Jeffamine® ED-900 (51.3 g, 0.057 mol) and triethylamine (11.74 g, 0.116 mol) in 500 mL of THF and 250 mL of chloroform was refluxed for 24 hours. Then the solid was filtered off, the mother filtrate was evaporated off to give a residue. The residue was purified by column flash chromatography to give the desired bis-(2-carboxymethoxythioxanthone) derivative of Jeffamine® ED-900 (60 g, 75% yield).

Example 6

Synthesis of mono-(2-carboxymethoxythioxanthone) derivative of Jeffamine® M-1000: A mixture of 2-thioxanthonyloxyacetic acid chloride (34.7 g, 0.114 mol), Jeffamine® M-1000 (114 g, 0.114 mol) and triethylamine (12 g, 0.118 mol) in 500 mL of THF and 250 mL of chloroform was refluxed for 24 hours. Then the solid was filtered off, the mother filtrate was evaporated off to give a residue. The residue was purified by column flash chromatography to give the desired mono-(2-carboxymethoxythioxanthone) derivative of Jeffamine® M-1000 (75 g, 75% yield).

Example 7

A UV or LED photo curable inkjet ink is prepared by mixing the following components as shown in Table 2.

TABLE 2

| Component | Weight Percent |
| --- | --- |
| UV reactive binder (photo active binder) | 15% |
| Irgacure ® 819 (co-photo initiator) | 0.3% |
| bis-(2-carboxymethoxythioxanthone) derivative of Jeffamine ® ED-900 (sensitizer or photo initiator) | 0.5% |
| LEG-1 (surfactant) | 1% |
| CT-211 (surfactant) | 1% |
| Crodafos ® N3 (anti-kogation agent) | 0.5% |
| Pigments | 2.5% |
| 2-hydroxyethyl-2-pyrrolidone (co-solvent) | 10% |
| Water | 69.2% |

Example 8

A UV or LED photo curable inkjet ink is prepared by mixing the following components as shown in Table 3.

TABLE 3

| Component | Weight Percent |
| --- | --- |
| UV reactive binder (photo active binder) | 15% |
| Irgacure ® 819 (co-photo initiator) | 0.3% |
| mono-(2-carboxymethoxythioxanthone) derivative of Jeffamine ® M-1000 (sensitizer or photo initiator) | 0.5% |
| LEG-1 (surfactant) | 1% |
| CT-211 (surfactant) | 1% |
| Crodafos ® N3 (anti-kogation agent) | 0.5% |
| Pigments | 2.5% |
| 2-hydroxyethyl-2-pyrrolidone (co-solvent) | 10% |
| Water | 69.2% |

Example 9

A UV or LED curable inkjet ink is prepared by mixing the following components as shown Table 4.

TABLE 4

| Component | Weight Percent |
| --- | --- |
| UV reactive binder | 5%∆ |
| Irgacure ® 819 (co-photo initiator) | 0.1% |
| bis-(2-carboxymethoxythioxanthone) derivative of Jeffamine ® ED-900 (sensitizer or photo initiator) | 0.25% |
| Aniline derivative of Jeffamine ® 900 (amine synergist) | 0.5% |
| LEG-1 (surfactant) | 1% |
| CT-211(surfactant) | 0.5% |
| Crodafos ® N3 (anti-kogation agent) | 0.5% |
| Pigments | 3% |
| 2-hydroxyethyl-2-pyrrolidone (co-solvent) | 10% |
| Water | 79.15% |

Example 10

A UV or LED curable inkjet ink is prepared by mixing the following components as shown in Table 5.

TABLE 5

| Component | Weight Percent |
| --- | --- |
| UV reactive binder | 10% |
| Irgacure ® 819 (photo initiator) | 0.2% |
| bis-(2-carboxymethoxythioxanthone) derivative of Jeffamine ® ED-900 (sensitizer or photo initiator) | 0.5% |
| LEG-1 (surfactant) | 1% |
| CT-211 (surfactant) | 1% |
| Crodafos ® N3 (anti-kogation agent) | 0.5% |
| Pigments | 4% |
| 2-hydroxyethyl-2-pyrrolidone (co-solvent) | 10% |
| Water | 72.5% |

Example 11

A UV or LED curable inkjet ink is prepared by mixing the following components as shown in Table 6.

TABLE 6

| Component | Weight Percent |
| --- | --- |
| UV reactive binder | 10% |
| Irgacure ® 819 (photo initiator) | 0.2% |
| bis-(2-carboxymethoxythioxanthone) derivative of Jeffamine ® ED-900 (sensitizer or photo initiator) | 1% |
| LEG-1 (surfactant) | 1% |
| CT-211 (surfactant) | 1% |
| Crodafos ® N3 (anti-kogation agent) | 0.5% |
| Pigments | 4% |
| 2-hydroxyethyl-2-pyrrolidone (co-solvent) | 10% |
| Water | 72% |

Example 12

A UV or LED curable inkjet ink is prepared by mixing the following components as shown in Table 7.

TABLE 7

| Component | Weight Percent |
| --- | --- |
| UV reactive binder | 10% |
| Irgacure ® 819 (photo initiator) | 0.2% |
| bis-(2-carboxymethoxythioxanthone) derivative of Jeffamine ® ED-900 (sensitizer or photo initiator) | 3% |
| LEG-1 (surfactant) | 1% |
| CT-211 (surfactant) | 1% |
| Crodafos ® N3 (anti-kogation agent) | 0.5% |
| Pigments | 4% |
| 2-hydroxyethyl-2-pyrrolidone (co-solvent) | 10% |
| Water | 70% |

Example 13

A UV or LED curable inkjet ink is prepared by mixing the following components as shown in Table 8.

TABLE 8

| Component | Weight Percent |
| --- | --- |
| UV reactive binder | 10% |
| Irgacure ® 819 (photo initiator) | 0.2% |
| bis-(2-carboxymethoxythioxanthone) derivative of Jeffamine ® ED-900 (sensitizer or photo initiator) | 5% |
| LEG-1 (surfactant) | 1% |
| CT-211 (surfactant) | 1% |
| Crodafos ® N3 (anti-kogation agent) | 0.5% |
| Pigments | 4% |
| 2-hydroxyethyl-2-pyrrolidone (co-solvent) | 10% |
| Water | 68% |

Example 14

A photo (UV LED) curable inkjet ink was prepared with the ingredients and proportions as in Example 8, using the following method: (1) Mix UV-curable polyurethane dispersion, 30% of the water amount and IRG819 PI dispersion at 60° C. for 5 min; (2) Mix 2HE2P, 70% of the water amount, Crodafos N3A, CT211, and LEG-1, then neutralize to pH=7.5 with KOH solution; (3) Combine the mixtures from steps (1) and (2); (4) Add mono-(2-carboxymethoxythioxanthone) derivative of Jeffamine® M-1000, mix well until it is dissolved into the mixture; (5) Mix (4) Into 14-SE-73 pigment dispersion; and (6) Adjust to pH=8.5 using KOH solution.

Example 15

A print test of the ink from Example 14 was performed using the following method: (1) Ink was filled into TIJ4 pen; (2) Fixer was printed from a different pen onto offset coated paper (Sterling Ultra Gloss "SUG"); (3) Ink was printed onto the paper; (4) Ink was immediately dried using hot air blower for 5 seconds at 375° F.; and (5) Dried ink was then immediately cured at a speed of 100 fpm using a 16 W/cm² LED 395 nm wavelength (from Phoseon).

Example 16

A wet rub test was performed 72 hr after printing. A Taber test tool was used with Crockmeier cloth attached to the tip. The weight load was 350 g. One cycle was performed. Water was used during the wet rub test. The delta optical density (ΔOD) was determined by measuring optical density before and after the rub. The lower the ΔOD, the better the durability. A ΔOD<0.15 is considered a very good score. The ink of Example 8 was printed and tested, and the same ink without the mono-(2-carboxymethoxythioxanthone) derivative of Jeffamine® M-1000 ("Control") was printed and tested. The results are shown in Table 9:

TABLE 9

| Wet Rub | Control | Example 8 |
| --- | --- | --- |
| ΔOD | 0.3 | 0.11 |

The results show that Example 8 ink which contained mono-(2-carboxymethoxythioxanthone) derivative of Jeffamine® M-1000 had ΔOD of 0.11 units compared to the control ink with higher ΔOD of 0.3 units. The inks' initial OD was 1.4 and 1.38 for Example 8 ink and the control ink respectively. The initial OD of both inks was thus similar and the ΔOD improvement shown is significant enough to suggest that the Example 8 ink that contained mono-(2-carboxymethoxythioxanthone) derivative of Jeffamine® M-1000 showed better wet rub durability compared to the control ink. This difference in durability can be attributed to an increased crosslinking degree by curing provided by adding mono-(2-carboxymethoxythioxanthone) derivative of Jeffamine® M-1000 sensitizer.

While the present technology has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:

1. A polymeric photo active agent, comprising a xanthone analog modified with a polyether chain connecting to the xanthone analog through an amide linkage, wherein the polyether chain includes polyethylene glycol, methoxypolyethylene glycol, polypropylene glycol, polybutylene glycol, or a copolymer thereof and wherein the polyether chain includes at least 5 monomer units, and wherein the polymeric photo active agent further comprises an additional xanthone analog moiety connecting to an opposite end of the polyether chain also through a second amide linkage.

2. The polymeric photo active agent of claim 1, wherein the xanthone analog with the amide linkage has the general formula:

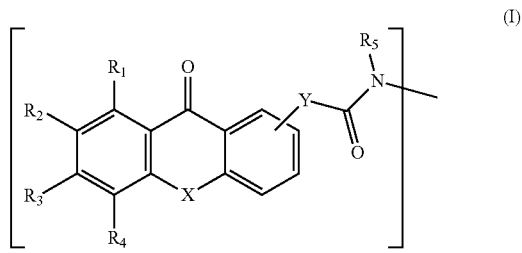

(I)

wherein $R_1$ to $R_5$ are independently selected from the group consisting of a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$, and a perfluoroalkyl group, wherein $R_d$, $R_e$, and $R_f$ are independently selected from the group consisting of a hydrogen atom, an unsubstituted alkyl, a substituted alkyl, an unsubstituted alkenyl, a substituted alkenyl, an unsubstituted aryl, a substituted aryl, an unsubstituted aralkyl, and a substituted aralkyl;

wherein X is selected from the group consisting of $-O-$, $-S-$, $-NH-$ and $-NR-$, wherein R is selected from the group consisting of $CH_3$, $CH_2CH_3$, and $CH_2CH_2CH_3$; and wherein Y is selected from the group consisting of a bond, $(CH_2)_q$, and $O(CH_2)_q$, wherein q is any integer from 1 to 100.

3. The polymeric photo active agent of claim 1, wherein the polyether chain is selected from the group consisting of polyethylene glycol, polypropylene glycol, and a copolymer of polyethylene glycol and polypropylene glycol.

4. The polymeric photo active agent of claim 1, having a general formula selected from the group consisting of:

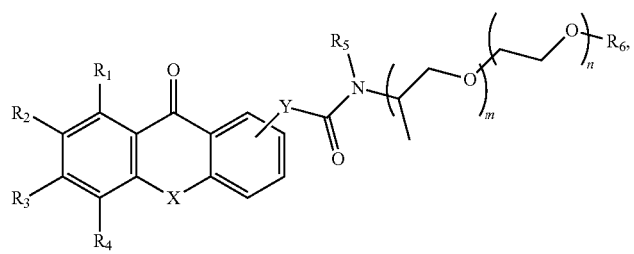
(II)
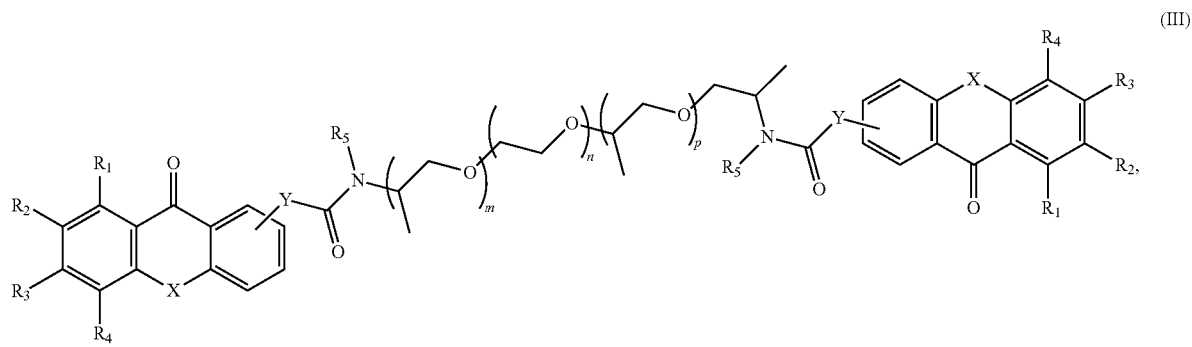
(III)
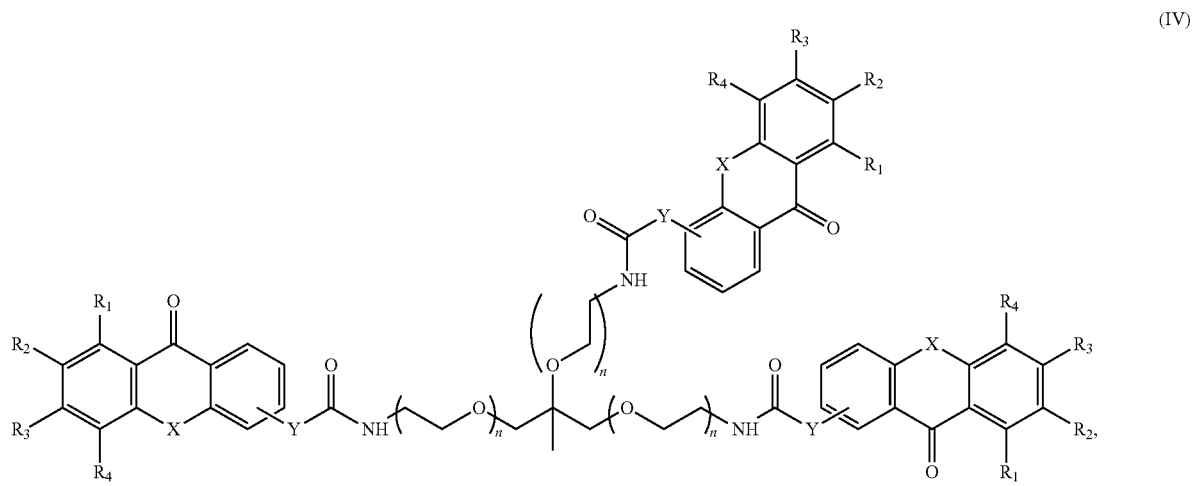
(IV)
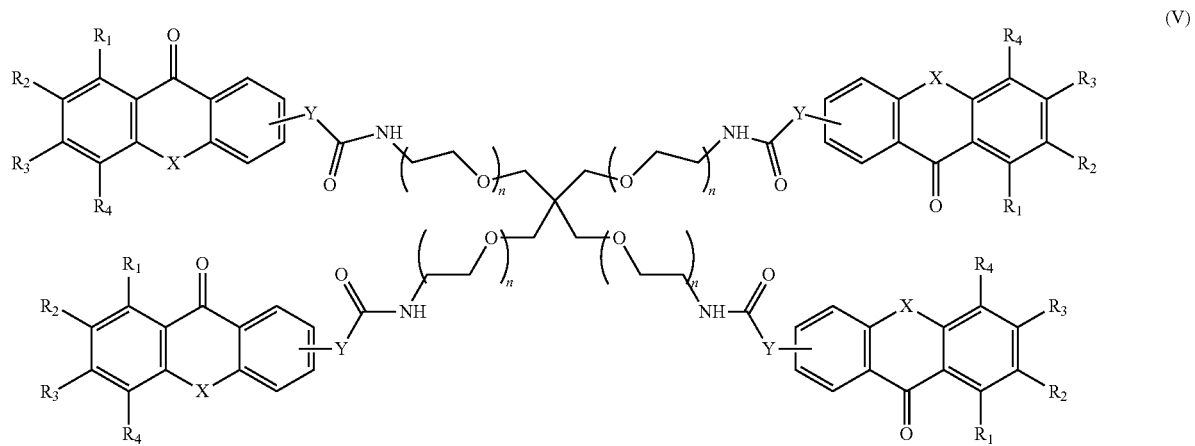
(V)

wherein $R_1$ to $R_6$ are independently selected from the group consisting of a hydrogen atom, an unsubstituted alkyl, a substituted alkyl, an unsubstituted alkenyl, a substituted alkenyl, an unsubstituted aryl, a substituted aryl, an unsubstituted aralkyl, a substituted aralkyl, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ and a perfluoroalkyl group, wherein $R_d$, $R_e$, and $R_f$ are independently selected from the group consisting of a hydrogen atom, an unsubstituted alkyl, a substituted alkyl, an unsubstituted alkenyl, a substituted alkenyl, an unsubstituted aryl, a substituted aryl, an unsubstituted aralkyl, and a substituted aralkyl;

wherein m, n, and p are independently any integer from 0 to 200, provided that the sum of m, n, and p is at least 5;

wherein X is selected from the group consisting of $-O-$, $-S-$, $-NH-$, and $-NR-$, wherein R is selected from the group consisting of $CH_3$, $CH_2CH_3$, and $CH_2CH_2CH_3$; and wherein Y is selected from the group consisting of a bond, $(CH_2)_q$, and $O(CH_2)_q$, wherein q is any integer from 1 to 100.

5. The polymeric photo active agent of claim 1, wherein the polymeric photo active agent has a molecular weight from about 500 Mw to about 5000 Mw.

6. The polymeric photo active agent of claim 1, having the formula

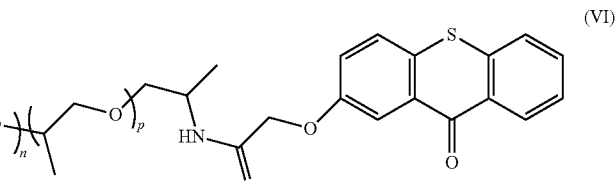

(VI)

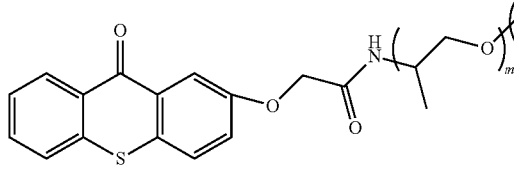

wherein m, n, and p are independently any integer provided that the sum of m, n, and p is from 10 to 25.

7. The polymeric photo active agent of claim 1, wherein the polymeric photo active agent is stable in water at a pH from 7 to 12.

8. The polymeric photo active agent of claim 1, wherein the polyether chain is derived from a polyethyleneoxy polypropyleneoxy chain portion of a polyethyleneoxy polypropyleneoxy amine.

9. The polymeric photo active agent of claim 1, wherein the polymeric photo active agent has a water solubility of at least 0.5 wt %.

10. A photo curable ink, comprising:
a photo reactive binder;
a polymeric photo active agent comprising a xanthone analog modified with a polyether chain connecting to the xanthone analog through an amide linkage, wherein the polyether chain includes polyethylene glycol, methoxypolyethylene glycol, polypropylene glycol, polybutylene glycol, or a copolymer thereof and wherein the polyether chain includes at least 5 monomer units, and wherein the polymeric photo active agent further comprises an additional xanthone analog moiety connecting to an opposite end of the polyether chain through a second amide linkage;
a co-photo initiator, a synergist, or combination thereof;
a colorant; and
a liquid vehicle including co-solvent and water.

11. The photo curable ink of claim 10, wherein the photo curable ink has a pH of 7 to 12, the polymeric photoactive agent is stable in the photo curable ink, and the photo curable ink is photo curable using UV LED electromagnetic radiation.

12. The photo curable ink of claim 10, wherein the polymeric photoactive agent is a sensitizer, and the ink comprises the co-photo initiator.

13. The photo curable ink of claim 10, wherein the polymeric photoactive agent is a photo initiator, and the ink comprises the synergist.

14. A method of making a photo curable ink, comprising mixing a photo reactive binder; a polymeric photo active agent comprising a xanthone analog modified with a polyether chain connecting to the xanthone analog through an amide linkage, wherein the polyether chain includes polyethylene glycol, methoxypolyethylene glycol, polypropylene glycol, polybutylene glycol, or a copolymer thereof and wherein the polyether chain includes at least 5 monomer units, and wherein the polymeric photo active agent further comprises an additional xanthone analog moiety connecting to an opposite end of the polyether chain through a second amide linkage; a co-photo initiator, a synergist, or combination thereof; a colorant; and a liquid vehicle including co-solvent and water.

15. A polymeric photo active agent having the formula
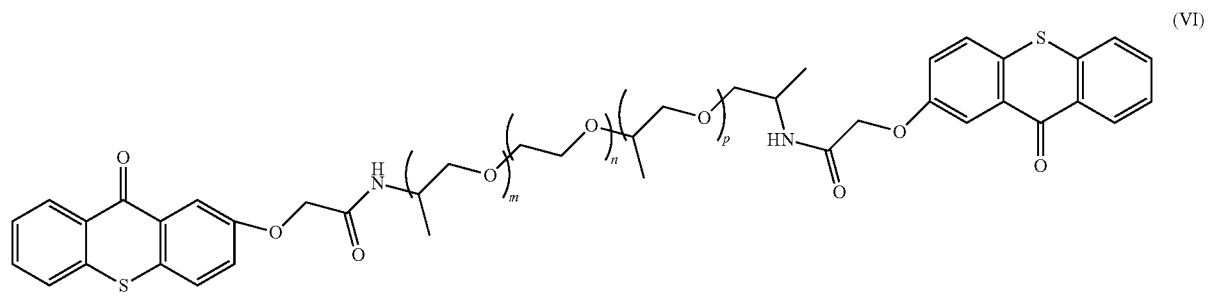
(VI)
wherein m, n, and p are independently any integer provided that the sum of m, n, and p is from 10 to 25.
* * * * *